US00PP15027P2

(12) United States Plant Patent

Anderson et al.

(10) Patent No.: US PP15,027 P2

(45) Date of Patent: Jul. 20, 2004

(54) CHRYSANTHEMUM PLANT NAMED 'MN98-M91-1'

(50) Latin Name: *Dendranthema×hybrida*
Varietal Denomination: MN98-M91-1

(75) Inventors: Neil Anderson, St. Paul, MN (US); Steve Poppe, Morris, MN (US); Esther Gesick, Maple Grove, MN (US); Peter Ascher, Bowler, WI (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 10/001,066

(22) Filed: Oct. 30, 2001

(51) Int. Cl.[7] ..... A01H 5/00

(52) U.S. Cl. ..... Plt./284

(58) Field of Search ..... Plt./295, 284

(56) References Cited

U.S. PATENT DOCUMENTS

| | | | |
|---|---|---|---|
| PP7,513 | P | 4/1991 | VandenBerg |
| PP7,754 | P | 12/1991 | VandenBerg |
| PP8,759 | P | 5/1994 | VandenBerg |
| PP9,445 | P | 1/1996 | VandenBerg |
| PP10,848 | P | 4/1999 | VandenBerg |
| PP10,909 | P | 5/1999 | Wain |
| PP10,943 | P | 6/1999 | Fuess |
| PP11,009 | P | 7/1999 | Davino, Jr. |
| PP11,032 | P | 8/1999 | Glicenstein |

OTHER PUBLICATIONS

Peter Ascher, et al., "Maxi–Mums A Horticultural Breakthrough!" Minnesota Report 242–1997 University of Minnesota, Distribution Center Publication MR–67280B Minnesota Agricultural Experiment Station, University of Minnesota (1997).

R.B. Clark, History of Culture of Hardy Chrysanthemums, National Chrysanthemum Society 18(3):144 (1962).

W.W. Garner, et al., Flowering and Fruiting of Plants as Controlled by the Length of Day, 1920, p. 377–400, Yearbook of the Department of Agriculture, 1920 USA.

Peter Ascher, et al., Breeding and New Cultivars, Academic Perspective, Tips on Growing and Marketing Garden Mums, Ohio Florists Association 1996.

Bradford Bearce et al., Chrysanthemums A Manual of the Culture, Diseases, Insects and Economics of Chrysanthemums, Jun. 1964, pp. 6–19, Prepared for The New York State Extension Service Chrysanthemum School with the Cooperation of the New York Flower Growers Association, Inc.

Neil O. Anderson, et al., Rapid Generation Cycling of Chrysanthemum Using Laboratory Seed Developmenta nd Embryo Rescue Techniques, Journal of the American Society of Horticultural Science, Mar. 1990, pp. 329–336, vol. 115(2), Alexandria, Virginia 22314.

Leon Glicenstein, Breeding and New Cultivars, Commercial Perspective, Tips on Growing and Marketing Garden Mums, Ohio Florist's Association 1996.

M.A. Nazeer, et al., Cytogenetical Evolution of Garden Chrysanthemum, Current Science, Jun. 20, 1982, vol. 51, No. 12.

Edward Higgins, Containers and Marketing, Tips on Growing and Marketing Garden Mums, Ohio Florists Association 1996.

Naomasa Himotomai, Bastardierungsversuche bei Chrysanthemum I., Journal of Science of Hiroshima University, Series B, Div. 2, vol. 1, Art. 3, 1931.

Naomasa Shimotomai, Bastardierungsversuche bei Chrysanthemum II. Eentstehung eines fruchtbaren Bastardes (haploid $4n^2$) aus der Kreuzung von *Ch. marginatum* (hapl. 5n) mit *Ch. morifolium* (hapl. 3n), Journal of Science of the Hiroshima University, Series B, Div. 2, vol. 1, Art. 8, 1932.

Ernest L. Scott, The Breeder's Handbook, 1957, pp. 1–76 Handbook No. 4, National Chrysanthemum Society, Inc., USA.

John Woolman, Chrysanthemums for Garden and Exhibition, 1953, pp. 1–103, W.H. & L. Collingridge Ltd., Tavistock Street, London WC2 and Transatlantic Arts Incorporated, Forest Hills, New York.

H.G. Witham Fogg, Chrysanthemum Growing, 1962, pp. 171, John Gifford Limited, London, W.C.2.

National Agricultural Statistics Service, USDA Additional Floriculture Information, pp. 1–84, National Agricultural Statistics Service, Floriculture Crops, 1998 Summary, Jun. 1999.

Handbook on Chrysanthemum Classification, A Publication of the Classification National Chrysanthemum Society, Inc., U.S.A., 1996 Edition.

C. Ackerson, Chapter 12, Development of the Chrysanthemum in China, pp. 146–155, National Chrysanthemum Society Bulletin 1967.

C. Ackerson, Chapter 11, Original Species of the Chrysanthemum, pp. 105–107, National Chrysanthemum Society Bulletin, 1967.

G.J. Dowrick, The Chromosomes of Chrysanthemum I: The Species, *Heredity*, 6:365–375 (1952).

Junyu, C., et al., *Acta Horticulturae*, 404:30–36 (1995).

*Primary Examiner*—Bruce R. Campell
*Assistant Examiner*—June Hwu
(74) *Attorney, Agent, or Firm*—Wood, Phillips, Katz, Clark & Mortimer

(57) ABSTRACT

A new and distinct chrysanthemum plant named MN98-M91-1 is provided. This new cultivar was the result of a cross between *Dendranthema weyrichii* and *Dendranthema×grandiflora*.

4 Drawing Sheets

Latin name of the genus and species of plant claimed: *Dendranthema×hybrida*.

Variety denomination: MN98-M91-1.

BACKGROUND OF THE INVENTION

The present invention comprises a new and distinctive chrysanthemum plant, hereinafter referred to by the cultivar name 'MN98-M91-1'. This new cultivar was the result of a cross in 1989 between *Dendranthema weyrichii* and *Dendranthema×grandiflora*. More specifically, the breeding program which resulted in the production of the new cultivar was carried out at St. Paul, Minn. The female or seed parent of 'MN98-M91-1' was a *Dendranthema weyrichii* 'Pink Bomb', commercially available from White Flower Farms, Conn. having the following characteristics: (a) the plant habit is prostrate and the plant spreads via rhizomes to form a large mat after the first year; (b) the plant dimensions are that the plant has a diameter of about 1.5' and is about 5–6" tall; (c) the plant is hardy in zones 4–9 (Southeast)/Zone 10 (west); (d) the flower of the plant is a single daisy, having light lavender-colored ray florets and central disc florets with yellow pollen; (e) the plant has leaves that are dark green in color, with a very shiny leaf surface (glossy), and glabrous leaf margins that are deeply incised; and (f) the plant tends to rosette, needs cold treatment to flower consistently, flowering can be sporadic with gaps in the plant architecture and the plant is an obligate short-day plant. The male or pollen parent of 'MN98-M91-1' was a *Dendranthema×grandiflora* which is commercially available from Yoder Brothers, Inc., Barberton, Ohio having the following characteristics: (a) the plant habit is cushion; (b) the plant dimensions are that the plant is similar to other cushion types commercially available from Yoder Brothers, Inc., such as, but not limited to the variety, 'Soft Cherie'; (c) the plant is hardy in zones 6–9 (Southeast)/Zone 10 (west); (d) the flower is a single or duplex daisy, possibly orange or bronze ray florets, central disc florets with yellow pollen; (f) the plant has leaves that are similar to other Yoder Brothers, Inc. cushion series chrysanthemums; and (d) the plant is a facultative short-day plant. The resulting seed, identified as 90-287-185 was collected. In 1994, a plant of 90-287-185 was crossed as the male parent with plants identified as 90-275-27, a University of Minnesota inbred parental selection, as the female parent and the resulting seeds, identified as cross number 92-333-3 collected. In 1997, a plant identified as 'Centerpiece' which is available from Dooley Gardens (Hutchinson, Minn.), was crossed as a male parent with plants of 95-332-3 and the resulting hybrid seeds constituted the cross 'MN98-M91-1' in which the genotype 'MN98-M91-1' was selected.

Asexual reproduction of the new cultivar by terminal or stem cuttings taken 1993 through 2000 at St. Paul, Minn., U.S.A. has demonstrated that the characteristics of the new cultivar as herein described are firmly fixed and are retained through successive generations of such asexual propagation.

SUMMARY OF INVENTION

It was found that the cultivar of the present invention:

(a) exhibits extreme hybrid vigor;

(b) develops, in its second and subsequent years after planting, when grown in the fall under natural day-length and without the application of growth regulators, into a flowering herbaceous shrub having a plant height of from about 2.75 to about 3.5 feet and a spread from about 4.0 to about 5.5 feet, (c) exhibits, in its second and subsequent years after planting and during the fall season (August–October), a massive floral display;

(d) exhibits superior winter hardiness, including frost tolerance; and (e) exhibits self-pinching.

The MN98-M91-1 cultivar has not been observed under all possible environmental condition to date. Accordingly, it is possible that the phenotype may vary somewhat with variations in the environment, such as temperature, light intensity, and day length.

When the new cultivar of the present invention is compared to 'Yellow Sandy' (U.S. Plant Pat. No. 8,759), it is found to exhibit a more spreading and prolific habit accompanied with a massive floral display in its second and subsequent years after planting. Reference is made to attached Table 1 below which compares certain characteristics of MN98-M91-1 to 'Yellow Sandy'.

TABLE 1

| CHARACTERISTIC | MN98-M91-1 | 'Yellow Sandy' |
|---|---|---|
| Plant Shape | cushion (mounded, spherical) | cushion |
| Plant height | | |
| (1st year) | 1.5' | 1.5–2' |
| (2nd year) | 2.75–3.5' | — (dead) |
| Flowering response | | |
| # weeks short days (SD) | 6.0 | 7.0 |
| Flower Type | Single daisy spoon | Duplex-Triplex Daisy |
| Flower Diameter | 8.3 cm | 7.0 cm |
| Ray florets, color, mature | | |
| Adaxial surface | RHS Yellow Group 3C | RHS Yellow Group 5A |
| Abaxial surface | RHS Yellow Group 5C | RHS Yellow Group 5A |

BRIEF DESCRIPTION OF THE PHOTOGRAPHS

The accompanying photographs show as nearly true as it is reasonably possible to make the same in color illustrations of this type, typical flower and foliage characteristics of the new cultivar. The plants were grown in a greenhouse at St. Paul, Minn., USA.

DETAILED BOTANICAL DESCRIPTION

Figure 1:
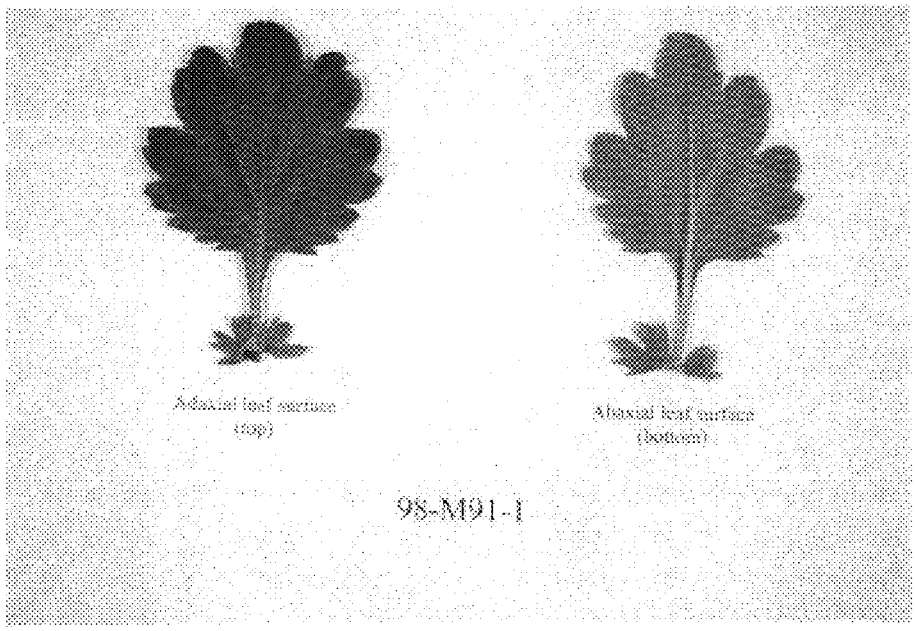
FIG. 1 shows an adaxial and abaxial view of the leaf shape of chrysanthemum variety MN98-M91-1.
Figure 2:
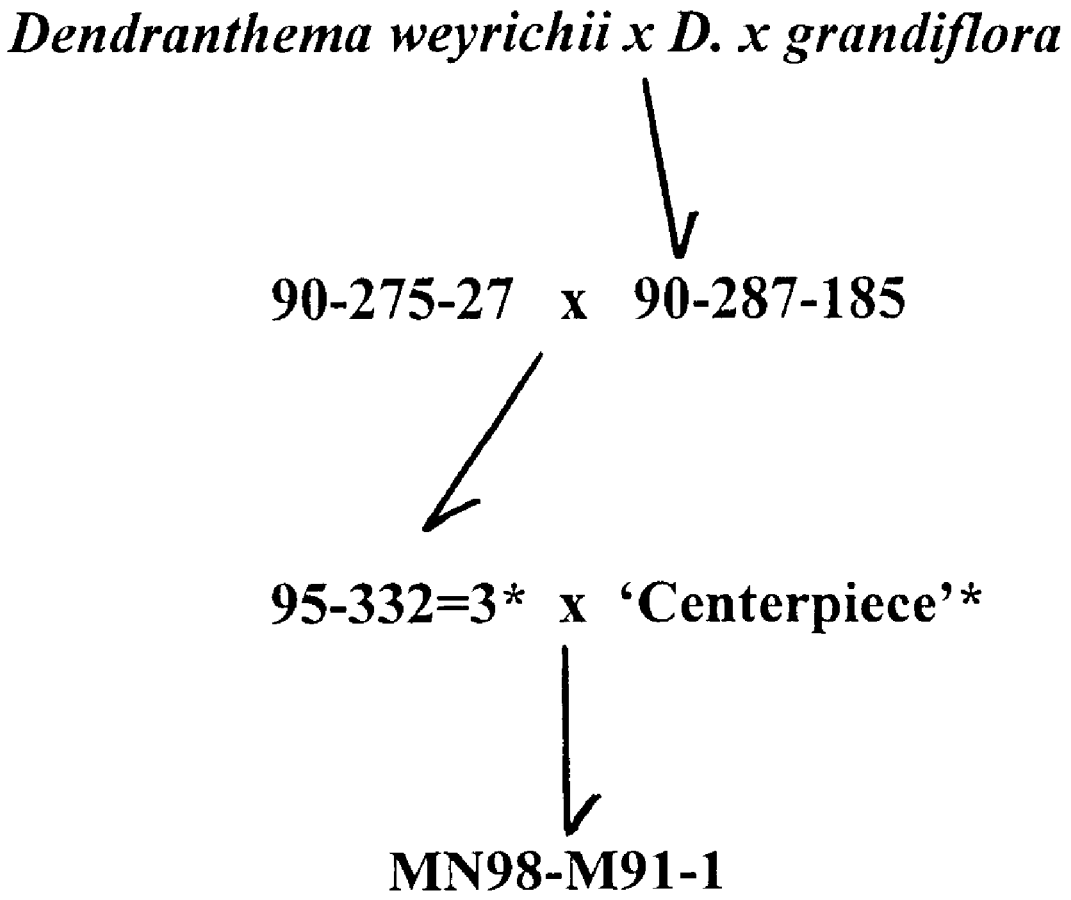
FIG. 2 shows the breeding history of chrysanthemum variety MN98-M91-1.
Figure 3:
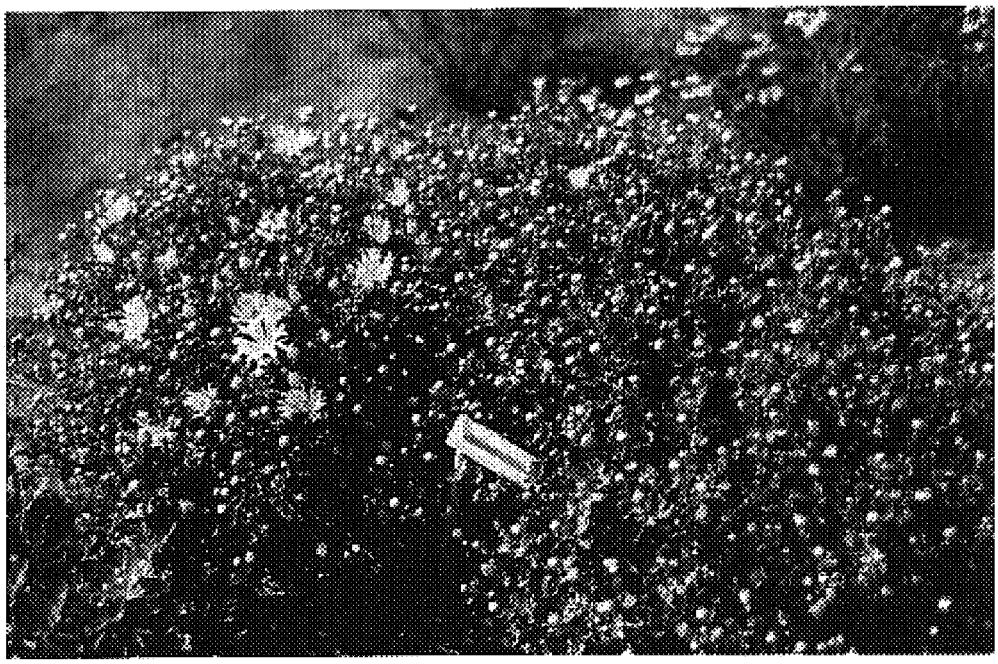
FIG. 3 is a color photograph of chrysanthemum variety MN98-M91-1 after one year of growth.
Figure 4:
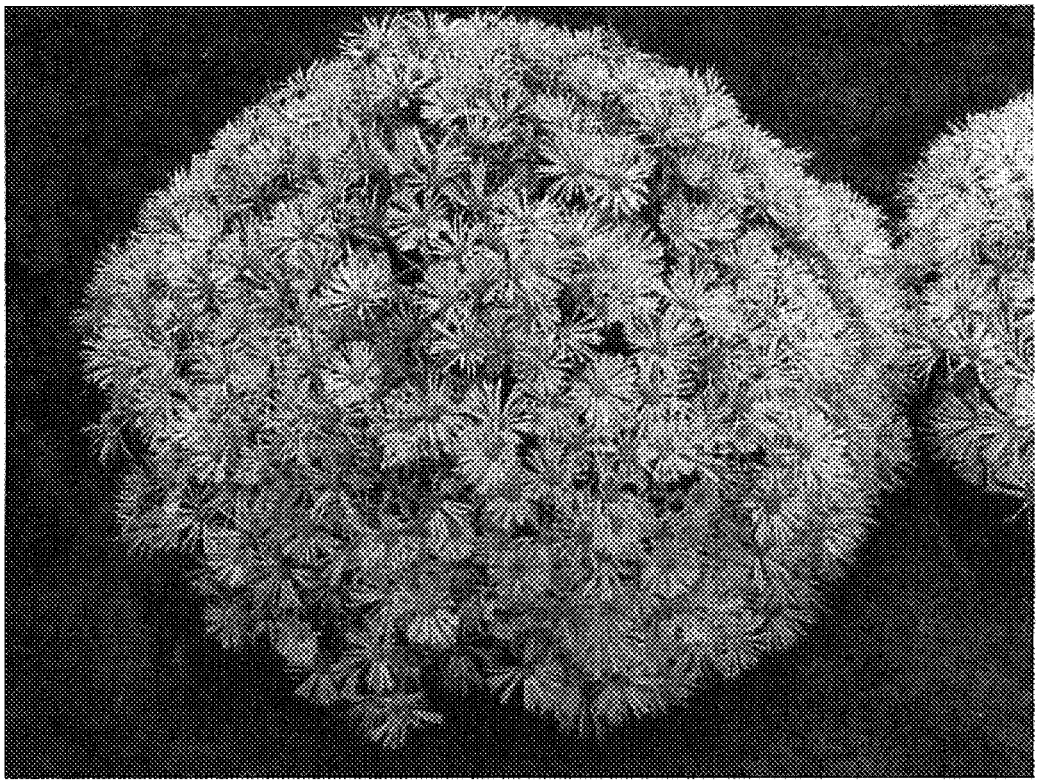
FIG. 4 is a color photograph of chrysanthemum variety MN98-M91-1 after two years of growth.

The chart used in the identification of colors described herein is The R.H.S. Colour Chart of The Royal Horticultural Society, London, England (1995 Edition). The color values were determined on Jan. 18, 2001 in St. Paul, Minn. The readings were taken between 1:00 and 3:00 p.m. under approximately 2500 footcandles of light. The plants were produced from cuttings taken from stock plants and were grown under greenhouse conditions comparable to those used in commercial practice while utilizing a soilness growth medium and maintaining temperatures of approximately 72° F. during the day and approximately 65° F. during the night.

Propagation:

*Type.*—Herbaceous stem cutting.

*Time to rooting.*—About 1 week.

*Rooting habit.*—Vigorous.

Plant description:

*Appearance, shape.*—Mounded spherical (first year). Mounded spherical (second year).

*Appearance, growth habit.*—Mound.

*Appearance, growth rate/vigor.*—Vigorous.

*Plant height.*—About 20 inches (first year). About 2.75–3.5 feet (second year) (estimated).

*Lateral branch length.*—About 14.5 inches.

*Quantity of lateral branches after removal of apical meristem.*—One per node.

*Stem color.*—RHS Greyed-Purple 183B, younger stems. RHS Yellow Green Group 152A, older stems.

Foliage description:

*Number of leaves per plant.*—Greater than 3,000 (second year).

*Number of leaves per lateral branch.*—5 to 19.

*Leaf arrangement.*—Alternate.

*Leaf size, fully expanded, lenth.*—7.4 cm.

*Leaf size, fully expanded width.*—4.4 cm.

*Leaf apex.*—Tri-mucronulate.

*Leaf base.*—Auriculate.

*Leaf margin.*—Incised (Mulberry-like incisions).

*Leaf texture.*—Fairly glaucous.

*Petiole length.*—3.1 cm.

*Color, young foliage adaxial surface.*—RHS Green Group 137B.

*Color, young foliage abaxial surface.*—RHS Green Group 137C.

*Color, fully expanded foliage adaxial surface.*—RHS Green Group 137A.

*Color, fully expanded foliage abaxial surface.*—RHS Yellow Green Group 147B.

*Color, venation adaxial surface.*—RHS Yellow Green Group 147C.

*Color, venation abaxial surface.*—RHS Yellow Green Group 148B.

*Color, petiole.*—RHS Yellow Green Group 148B.

Phyllary description:

*Appearance.*—The involucral bracts (phyllaries) are crenulate.

*Color.*—RHS Green Group 137A.

*Texture.*—Glabrous.

*Size.*—Approximately 0.2–0.4 cm in length.

Inflorescene description:

*Appearance.*—Head (composite), single daisy spoon.

*Flowering response.*—About 6.0 weeks (short day) (estimates).

*Quantity of inflorescences.*—About 500 (first year). Greater than 3,500 (second year).

*Inflorescence size, diameter.*—8.3 cm.

*Inflorescence size, depth (height)*—1.7 cm.

*Inflorescence size, diameter of disc.*—1.5 cm.

*Opening inflorescences, bud shape.*—Twisted petals, upright.

*Opening inflorescences, bud size, length.*—2.5 cm.

*Opening inflorescences, bud size, width.*—1.4 cm.

*Opening inflorescences, bud color.*—RHS Yellow Group 5C.

*Ray florets, shape.*—Spoon.

*Ray florets, size, length.*—3.9 cm.

*Ray florets, size, width.*—0.4 cm.

*Ray florets, apex.*—Bi-retuse.

*Ray florets, base.*—Attenuate.

*Ray florets, margin.*—Entire, tubular (quilled).

*Ray florets, texture.*—Glabrous.

*Ray florets, aspect.*—About 45°.

*Number of ray florets per inflorescence.*—About 36.6.

*Ray florets, color, when opening, adaxial surface.*—RHS Yellow Group 3A.

*Ray florets, color, when opening, abaxial surface.*—RHS Yellow Group 4B.

*Ray florets, color, mature, adaxial surface.*—RHS Yellow Group 3C.

*Ray florets, color, mature, adaxial surface.*—RHS Yellow Group 5C.

*Ray florets, color, fading to.*—RHS Yellow Group 3C.

*Disc florets, shape.*—Tubular, rounded at tip.

*Disc florets, size, length.*—0.5 cm.

*Disc florets, size, width.*—0.1 cm.

*Number of disc florets per inflorescence.*—About 115.

*Disc florets, color, immature.*—RHS Yellow Group 4C.

*Disc florets, color, mature.*—RHS Yellow Orange Group 15A.

*Peduncle, aspect, strength.*—Stiff.

*Peduncle, aspect, angle to stem.*—45°.

*Peduncle, length, first peduncle.*—3.3 cm.

*Peduncle, length, fourth peduncle.*—4.9 cm.

*Peduncle, texture.*—Hirsute.

*Peduncle, color.*—RHS Green Group 131C.

*Reproductive organs, androecium, floret location.*—Disc florets.

*Anther color.*—RHS Yellow Orange Group 16A.

*Pollen, abundance.*—Abundant.

*Pollen, color.*—RHS Yellow Orange Group 16A.

*Reproductive organs, gynoecium, floret location.*—Disc/ray florets.

*Style color.*—RHS Yellow Group 11D.

*Stamen description.*—Stamens are located within each individual disk floret. Each stamen is borne on a filament that, when mature (dihiscent with pollen shedding longitudinally along the length axis of the anther), places the stamens above the stigma (i.e., the top portion of the pistil.)

*Pistil number.*—Each ray floret possesses one pistil (there are approximately 60 per inflorescence). Likewise, each disk floret also possesses a pistil (there are approximately 191 per inflorescence). Therefore, the total number of pistils/inflorescence is 251 (60+191). The size of the pistil (length) is approximately 1 cm.

*Disease resistance.*—None known as 'MN98-M91-1' has not been tested for any diseases.

*Seed production and fruit.*—About 152 ovules/flower. The fruit is an achene, a dry, indehiscent fruit with a single locule and a single seed, and with the seed attached to the ovary wall at a single point. The achene does not have any pappus of awns for bristles; its general shape is a half-inflated football oval with pointed ends. Seed size is about 0.2–0.5 cm in length and about 0.1–0.2 cm in width. The surface texture is ridged. The color designation for the seed is RHS Brown Group 200D.

*Fragrance.*—Fragrance is noticeable when handling or bruising the foliage.

*Longevity of the bloom.*—Flower longevity is temperature dependent. Under normal conditions in the field, during the fall season, flowers will typically last about 2–4 plus weeks.

What is claimed is:

1. A new and distinct chrysanthemum plant as herein described and illustrated.

* * * * *